US012673123B2

(12) United States Patent
Kotani et al.

(10) Patent No.: US 12,673,123 B2
(45) Date of Patent: Jul. 7, 2026

(54) ENDOSCOPE CART AND INSTRUMENT FOR ENDOSCOPE

(71) Applicant: FUJIFILM Corporation, Tokyo (JP)

(72) Inventors: Kojiro Kotani, Kanagawa (JP); Yutaka Senda, Kanagawa (JP); Shozo Iyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 360 days.

(21) Appl. No.: 18/318,690

(22) Filed: May 16, 2023

(65) Prior Publication Data

US 2023/0285614 A1 Sep. 14, 2023

Related U.S. Application Data

(63) Continuation of application No. PCT/JP2021/040968, filed on Nov. 8, 2021.

(30) Foreign Application Priority Data

Nov. 19, 2020 (JP) .................................. 2020-192470

(51) Int. Cl.
*A61L 2/10* (2026.01)
*A61B 50/13* (2016.01)
(Continued)

(52) U.S. Cl.
CPC ................ *A61L 2/10* (2013.01); *A61B 50/13* (2016.02); *A61B 90/70* (2016.02); *A61L 2/26* (2013.01);
(Continued)

(58) Field of Classification Search
CPC .......... A61L 2/10; A61L 2/26; A61L 2202/11; A61L 2202/121; A61L 2202/122;
(Continued)

(56) References Cited

U.S. PATENT DOCUMENTS 4,772,795 A * 9/1988 Sakurai ................ A61C 19/002
250/455.11
6,039,928 A * 3/2000 Roberts ..................... A61L 2/10
422/186.3
(Continued)

FOREIGN PATENT DOCUMENTS

CN 204951457 1/2016
CN 207640493 7/2018
(Continued)

OTHER PUBLICATIONS

"International Search Report (Form PCT/ISA/210) of PCT/JP2021/040968," mailed on Jan. 18, 2022, pp. 1-2.
(Continued)

*Primary Examiner* — Wyatt A Stoffa
(74) *Attorney, Agent, or Firm* — JCIPRNET

(57) ABSTRACT

On a shelf plate constituting a placement portion, the instrument for an endoscope is placed. An ultraviolet ray source portion irradiates the instrument for an endoscope with ultraviolet rays. A handle portion is provided with an ultraviolet ray source portion and a drawer portion is provided with an ultraviolet ray source portion. A rotary panel is provided with an ultraviolet ray source portion. An ultraviolet ray source unit including an ultraviolet ray source portion is provided on a side surface of the shelf plate.

9 Claims, 14 Drawing Sheets

(51) Int. Cl.
| | |
|---|---|
| *A61B 90/70* | (2016.01) |
| *A61L 2/26* | (2006.01) |
| *A61L 103/15* | (2026.01) |

(52) U.S. Cl.
CPC ..... *A61B 2090/701* (2016.02); *A61L 2103/15* (2026.01); *A61L 2202/11* (2013.01); *A61L 2202/121* (2013.01); *A61L 2202/122* (2013.01); *A61L 2202/16* (2013.01)

(58) Field of Classification Search
CPC . A61L 2202/16; A61L 2202/24; A61B 50/13; A61B 50/33; A61B 90/70; A61B 2090/701
See application file for complete search history.

(56) References Cited

U.S. PATENT DOCUMENTS

| | | | | |
|---|---|---|---|---|
| 6,171,559 | B1 * | 1/2001 | Sanders | A61L 2/18 |
| | | | | 134/144 |
| 6,258,736 | B1 * | 7/2001 | Massholder | A61L 2/10 |
| | | | | 438/795 |
| 6,605,260 | B1 * | 8/2003 | Busted | A61L 2/10 |
| | | | | 422/186.3 |
| 9,364,573 | B2 * | 6/2016 | Deshays | A61L 2/24 |
| 9,550,006 | B2 * | 1/2017 | Boodaghians | A61L 2/10 |
| 9,907,870 | B2 * | 3/2018 | Boodaghians | A61L 2/10 |
| 10,517,974 | B2 * | 12/2019 | Dobrinsky | G02B 5/10 |
| 10,856,952 | B2 * | 12/2020 | Bauco | A61B 90/70 |
| 11,331,399 | B2 * | 5/2022 | Mansell | A61B 50/13 |
| 11,974,721 | B2 * | 5/2024 | Jackson | A61B 1/00144 |
| 2002/0162972 | A1 * | 11/2002 | Pleet | A61B 90/70 |
| | | | | 250/492.1 |
| 2006/0013454 | A1 * | 1/2006 | Flewelling | G06T 11/00 |
| | | | | 382/128 |
| 2007/0239000 | A1 * | 10/2007 | Emery | A61B 8/0833 |
| | | | | 600/437 |
| 2008/0149001 | A1 | 6/2008 | Hodges et al. | |
| 2008/0283769 | A1 * | 11/2008 | Deshays | A61L 2/24 |
| | | | | 250/455.11 |
| 2009/0191100 | A1 * | 7/2009 | Deal | A61L 2/10 |
| | | | | 422/105 |
| 2009/0206674 | A1 * | 8/2009 | Noguchi | A61B 50/10 |
| | | | | 307/104 |
| 2009/0304553 | A1 * | 12/2009 | Gordon | A61L 2/10 |
| | | | | 422/186 |
| 2011/0054574 | A1 * | 3/2011 | Felix | A61N 5/06 |
| | | | | 250/493.1 |

| | | | | |
|---|---|---|---|---|
| 2011/0256019 | A1 * | 10/2011 | Gruen | A61L 2/10 |
| | | | | 345/173 |
| 2012/0230867 | A1 * | 9/2012 | Kerr | A61L 2/10 |
| | | | | 422/292 |
| 2013/0062534 | A1 * | 3/2013 | Cole | A61N 5/0624 |
| | | | | 250/454.11 |
| 2014/0059796 | A1 * | 3/2014 | Boodaghians | A61L 2/10 |
| | | | | 250/455.11 |
| 2014/0356229 | A1 * | 12/2014 | Farren | A61L 2/10 |
| | | | | 250/492.1 |
| 2016/0324996 | A1 * | 11/2016 | Bilenko | A61L 2/10 |
| 2018/0104368 | A1 * | 4/2018 | Dobrinsky | A61L 2/10 |
| 2018/0178823 | A1 * | 6/2018 | Yang | A61L 2/10 |
| 2018/0250428 | A1 * | 9/2018 | Canfield | A61L 2/10 |
| 2020/0215212 | A1 * | 7/2020 | Mansell | A61B 50/13 |
| 2021/0338863 | A1 * | 11/2021 | Hammad | A61L 2/10 |
| 2022/0062466 | A1 * | 3/2022 | Lee | A61L 2/10 |
| 2022/0063471 | A1 * | 3/2022 | Sakurai | B60N 3/026 |
| 2022/0096678 | A1 * | 3/2022 | Kea | A61L 2/10 |
| 2022/0193281 | A1 * | 6/2022 | Dencovski | A61L 2/10 |
| 2022/0253056 | A1 * | 8/2022 | Ranjan | A61L 2/10 |
| 2023/0012667 | A1 * | 1/2023 | Asimus | A61L 2/26 |
| 2023/0022861 | A1 * | 1/2023 | Cole | A61L 2/24 |
| 2023/0285615 | A1 * | 9/2023 | Kotani | A61B 1/122 |

FOREIGN PATENT DOCUMENTS

| | | |
|---|---|---|
| CN | 209332000 | 9/2019 |
| CN | 209404952 | 9/2019 |
| JP | S860212141 | 10/1985 |
| JP | H0595888 | 4/1993 |
| JP | H05103747 | 4/1993 |
| JP | H10309262 | 11/1998 |
| JP | 2007050240 | 3/2007 |
| JP | 2007075392 | 3/2007 |
| JP | 2012135471 | 7/2012 |

OTHER PUBLICATIONS

"Written Opinion of the International Searching Authority (Form PCT/ISA/237) of PCT/JP2021/040968," mailed on Jan. 18, 2022, pp. 1-4.
"Office Action of Japan Counterpart Application", issued on Jun. 24, 2025, with English translation thereof, pp. 1-8.
"Office Action of China Counterpart Application", issued on Jul. 25, 2025, with English translation thereof, pp. 1-16.
"The Third Office Action of China Counterpart Application", issued on Mar. 27, 2026, with English translation thereof, p. 1-p. 17.

* cited by examiner

ENDOSCOPE CART AND INSTRUMENT FOR ENDOSCOPE

CROSS-REFERENCE TO RELATED APPLICATIONS

This application is a Continuation of PCT International Application No. PCT/JP2021/040968 filed on 8 Nov. 2021, which claims priority under 35 U.S.C § 119(a) to Japanese Patent Application No. 2020-192470 filed on 19 Nov. 2020. The above application is hereby expressly incorporated by reference, in its entirety, into the present application.

BACKGROUND OF THE INVENTION

1. Field of the Invention

The present invention relates to an endoscope cart and an instrument for an endoscope.

2. Description of the Related Art

In the medical field, a digestive tract and the like is observed by means of an endoscope. In the case of observation performed by means of an endoscope, a user such as a doctor, a technologist, and a nurse operates an endoscope instrument such as the endoscope, a light source device, and a processor device by directly touching the endoscope instrument. In order to prevent infection caused by pathogenic bacterium or viruses accompanied by the contact between the user and the endoscope instrument, the endoscope instrument is bacteria-eliminated or sterilized before a test or the like.

For example, in JP1998-309262A (JP-H10-309262A), a plurality of coating members are stacked on an operation portion of a front panel of a light source device or a processor device and the coating members are stripped off after a test so that cleanliness is maintained. In addition, in JP2012-135471A, the entire surface of a touch panel, which is a front surface of an endoscope processor, is covered with a film set and a film is stripped off after a test so that time and effort for cleaning or disinfection are saved. In addition, regarding an endoscope cart in JP2007-75392A, a monitor is covered with a hood and at least a front surface of an instrument for an endoscope such as a processor placed on the cart is covered with a screen curtain so that dust is prevented from adhering to the instrument for an endoscope or the like in a case where endoscopy is not performed.

SUMMARY OF THE INVENTION

In a case where a covering member or a film is used as in JP1998-309262A (JP-H10-309262A) or JP2012-135471A, it is troublesome to perform replacement for each time a test is performed. In addition, it may not be possible to determine whether or not the covering member or the like has already been replaced. Furthermore, the covering member or the like stripped off needs to be subjected to a discarding process, and measures for prevention of infection need to be taken in the discarding process. In addition, regarding JP2007-75392A, the hood or the screen curtain needs to be open throughout the test and thus droplets and the like may adhere to the instrument for an endoscope. In this case, viruses or the like adhering to the instrument for an endoscope or the like cannot be removed. Therefore, there is a demand for a technique with which it is possible to sterilize an instrument for an endoscope even in a case where droplets or the like adhere to the instrument for an endoscope instead of a technique of preventing the droplets and the like from adhering to the instrument for an endoscope.

An object of the present invention is to provide an endoscope cart and an instrument for an endoscope with which it is possible to sterilize the instrument for an endoscope even in a case where droplets and the like adhere to the instrument for an endoscope.

An endoscope cart according to an aspect of the present invention includes a placement portion on which an instrument for an endoscope is placed and an ultraviolet ray source portion that irradiates the instrument for an endoscope with ultraviolet rays.

It is preferable that the endoscope cart further includes a top plate that is provided above the placement portion and a handle portion provided at a front portion of the top plate and the handle portion is provided with the ultraviolet ray source portion. It is preferable that the endoscope cart further includes a top plate that is provided above the placement portion and a drawer portion that is provided between the top plate and the placement portion and that includes a sliding plate movable between a storage position and a pull-out position to which the sliding plate is pulled out from the storage position and the sliding plate is provided with the ultraviolet ray source portion. It is preferable that the instrument for an endoscope is irradiated with the ultraviolet rays from at least one of an upper side or an obliquely upper side.

It is preferable that the endoscope cart further includes a top plate that is provided above the placement portion, a drawer portion that is provided between the top plate and the placement portion and that includes a sliding plate movable between a storage position and a pull-out position to which the sliding plate is pulled out from the storage position, and a rotary panel that is attached to the sliding plate to be rotatable between a closing position and an opening position, and the rotary panel is provided with the ultraviolet ray source portion.

It is preferable that the endoscope cart further includes an ultraviolet ray source unit composed of a light source housing that is provided with the ultraviolet ray source portion and a light source holding portion that holds the light source housing, that is movable in a first direction, and that is rotatable toward a second direction orthogonal to the first direction.

It is preferable that the ultraviolet ray source portion includes an ultraviolet ray source that emits the ultraviolet rays and an emission portion through which the ultraviolet rays are emitted toward the instrument for an endoscope, and the ultraviolet ray source and the emission portion face each other. It is preferable that the ultraviolet ray source portion includes an ultraviolet ray source that emits the ultraviolet rays, a light guide plate that guides the ultraviolet rays emitted from the ultraviolet ray source, and an emission portion through which the ultraviolet rays are emitted toward the instrument for an endoscope, and the light guide plate and the emission portion face each other.

It is preferable that the ultraviolet ray source is any of an excimer lamp or an LED. It is preferable that the instrument for an endoscope is any one or a combination of two or more of a processor device, a light source device, a balloon controller, a water supply device, an air supply device, a navigation device, a diagnosis support device, an ultrasonic observation device, or a treatment tool power source.

An instrument for an endoscope according to another aspect of the present invention includes an ultraviolet ray source portion that performs irradiation with ultraviolet rays.

It is preferable that the instrument for an endoscope further includes an ultraviolet ray source unit composed of a light source housing that is provided with the ultraviolet ray source portion and a light source holding portion that holds the light source housing, that is movable in a first direction, and that is rotatable toward a second direction orthogonal to the first direction.

It is preferable that the ultraviolet ray source portion includes an ultraviolet ray source that emits the ultraviolet rays and an emission portion through which the ultraviolet rays are emitted toward the instrument for an endoscope, and the ultraviolet ray source and the emission portion face each other. It is preferable that the ultraviolet ray source portion includes an ultraviolet ray source that emits the ultraviolet rays, a light guide plate that guides the ultraviolet rays emitted from the ultraviolet ray source, and an emission portion through which the ultraviolet rays are emitted toward the instrument for an endoscope, and the light guide plate and the emission portion face each other.

It is preferable that the ultraviolet ray source is any of an excimer lamp or an LED. It is preferable that the instrument for an endoscope is any one or a combination of two or more of a processor device, a light source device, a cleaning and disinfecting apparatus, a balloon controller, a water supply device, an air supply device, a navigation device, a diagnosis support device, an ultrasonic observation device, or a treatment tool power source.

According to the aspects of the present invention, it is possible to sterilize an instrument for an endoscope even in a case where droplets and the like adhere to the instrument for an endoscope.

DESCRIPTION OF THE PREFERRED EMBODIMENTS

Figure 1:
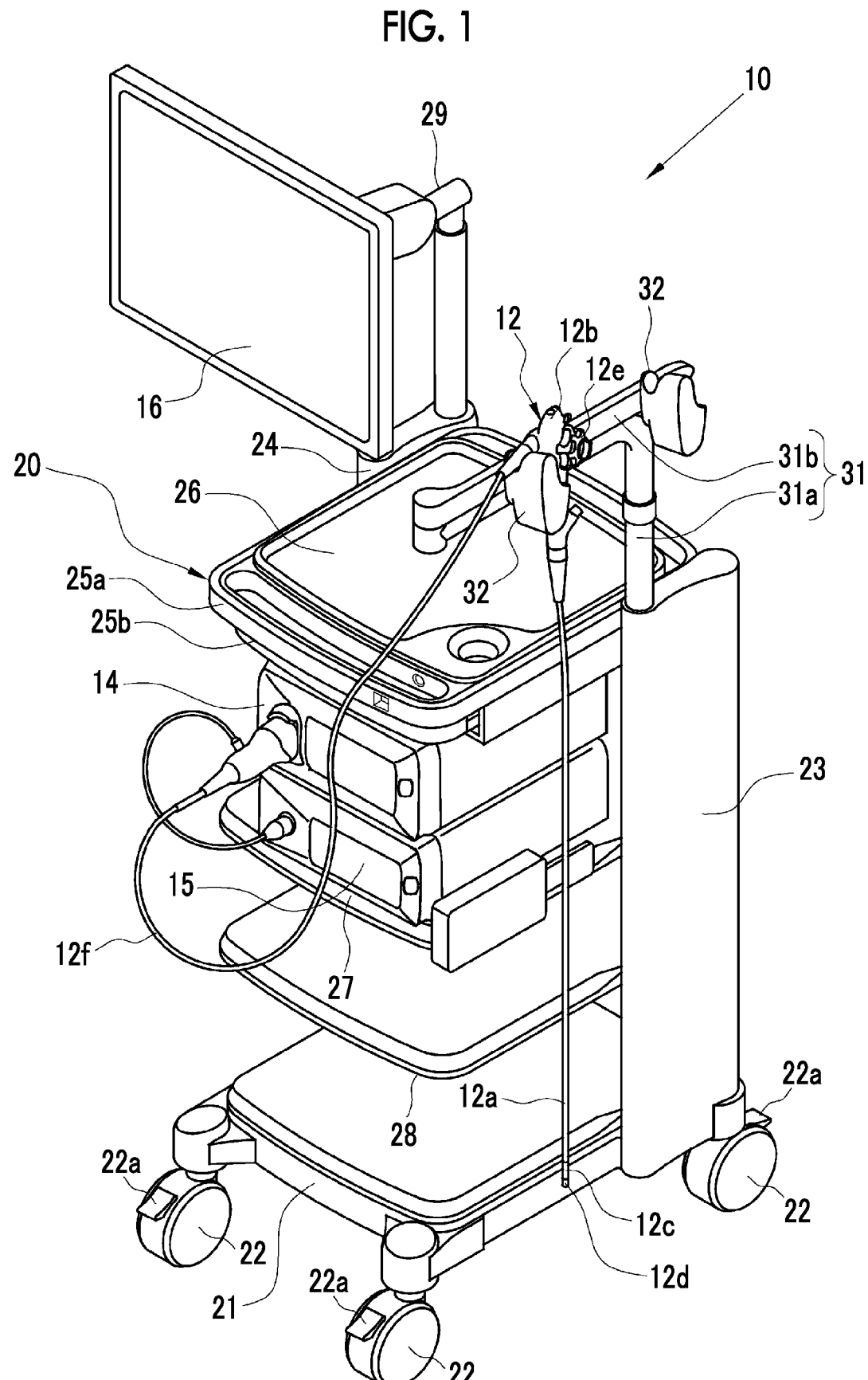
FIG. 1 is a perspective view of an endoscope system and an endoscope cart.

As shown in FIG. 1, an endoscope system 10 includes an endoscope 12, a light source device 14, a processor device 15, a display 16, and an endoscope cart 20 on which these devices are placed to be transported. The endoscope 12 images an observation target. The light source device 14 emits illumination light with which the observation target is irradiated. The processor device 15 controls the endoscope system 10. The display 16 is a display unit that displays an observation image or the like based on an endoscopic image.

The endoscope 12 includes a soft portion 12a, an operation portion 12b provided at a proximal end portion of the soft portion 12a, a bendable portion 12c provided on a distal end side of the soft portion 12a, and a distal end portion 12d. In a case where an angle knob 12e of the operation portion 12b is operated, the bendable portion 12c is bent. As a result, the distal end portion 12d faces a desired direction. The endoscope 12 includes a cord 12f connected to the light source device 14 and the processor device 15, is optically connected to the light source device 14, and is electrically connected to the processor device 15. Note that an insertion portion of the endoscope 12 is composed of the soft portion 12a, the bendable portion 12c, and the distal end portion 12d.

The endoscope cart 20 includes a frame pedestal portion 21, four casters 22, columns 23 and 24, a top plate 26, shelf plates 27 and 28, a stand 29, and two hangers 32. The frame pedestal portion 21 is formed in an approximately rectangular shape and the casters 22 are provided at four corners thereof. The columns 23 and 24 are columnar members that are erected to extend upward from both of side end portions of the frame pedestal portion 21. The top plate 26 is formed in an approximately rectangular shape and is disposed at upper ends of the columns 23 and 24. Both of side end portions of the top plate 26 are fixed to inner sides of upper end portions of the columns 23 and 24.

The shelf plates 27 and 28 are placement portions on which an instrument for an endoscope or the like is placed. The shelf plates 27 and 28 are formed in an approximately rectangular shape and are fixed to inner sides of intermediate portions of the columns 23 and 24. Examples of the instrument for an endoscope include a balloon controller, a water supply device, an air supply device, a navigation device, a diagnosis support device, an ultrasonic observation device, and a treatment tool power source in addition to the light source device 14 and the processor device 15.

The shelf plates 27 and 28 partition a space between the frame pedestal portion 21 and the top plate 26. Each caster 22 is provided with a stop lever 22a for restriction of rotation of the caster 22. The rotation of the caster 22 is restricted in a case where the stop lever 22a is in a raised state and the rotation of the caster 22 is allowed in a case where the stop lever 22a is in a lowered state.

The top plate 26 and the shelf plates 27 and 28 are panels with upper surfaces on which the instrument for an endoscope or the like is to be placed and in an example shown in FIG. 1, the processor device 15 and the light source device 14 are placed on an upper surface of the shelf plate 27.

A front portion of the top plate 26 is provided with a handle portion 25a. A user can easily move the endoscope cart 20 while holding the handle portion 25a with a hand. A drawer portion 25b that is movable between a storage position (a state shown in FIG. 2) and a pull-out position to which the drawer portion 25b is pulled out from the storage position (a state shown in in FIG. 4) is provided between the top plate 26 and the shelf plate 27. A keyboard 30 (refer to FIGS. 4 and 5) that is used for input to the processor device 15 or the like is stored in the drawer portion 25b. The display 16 is fixed to the stand 29 attached to an upper end of the column 24 on the left side, and is connected to the processor device 15 via a wiring line in the stand 29 and the column 24.

A hanger stand 31 is attached to the upper end of the column 23 on the right side. The hanger stand 31 is composed of an L-shaped stand member 31a and a linear stand member 31b. One end portion of the stand member 31a is rotatably attached to the column 23. The two hangers 32 are fixed to the stand member 31b. Each hanger 32 includes a notch portion or a groove, and the endoscope 12 can be hung on the hanger 32 with the operation portion 12b of the endoscope 12 being held at the notch portion or the groove.

The stand member 31b is rotatably connected to the other end portion of the stand member 31a. Accordingly, it is possible to adjust the position of the endoscope 12 held by the hangers 32 by rotating the stand members 31a and 31b with respect to the column 23.

Figure 2:
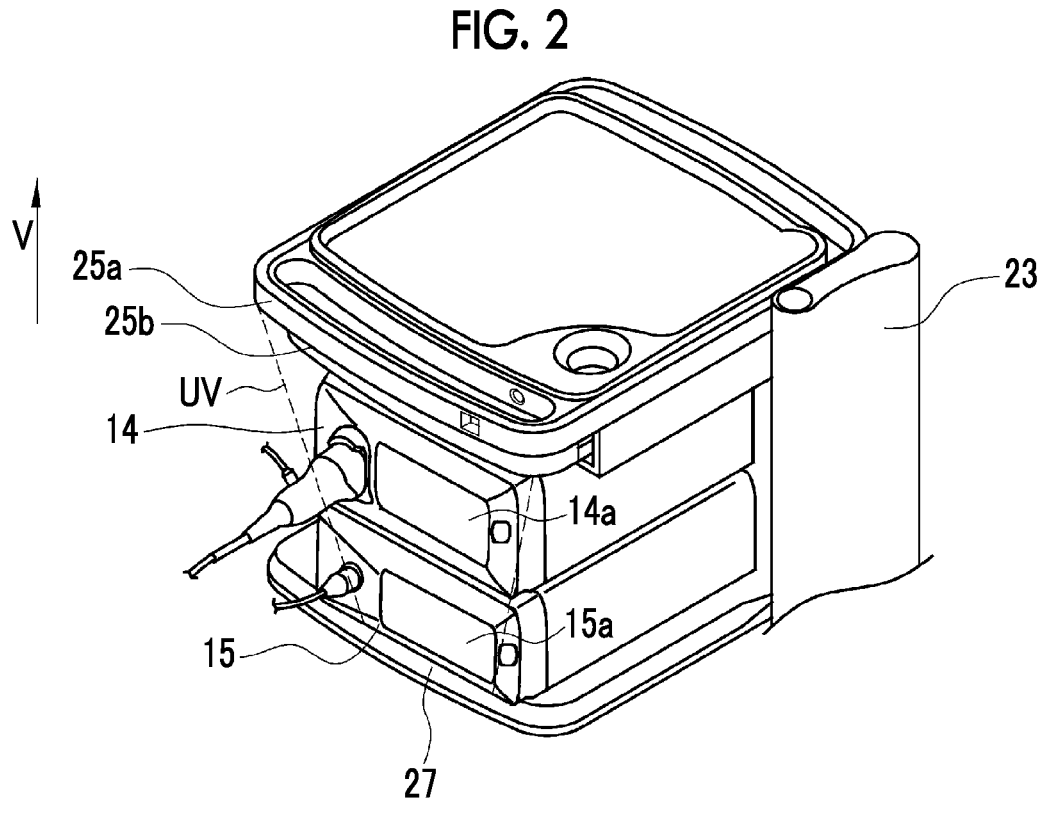
FIG. 2 is a perspective view of a light source device, a processor device, and a placement portion, on which the light source device and the processor device are mounted, in a case where a handle portion is provided with an ultraviolet ray source portion.
Figure 3:
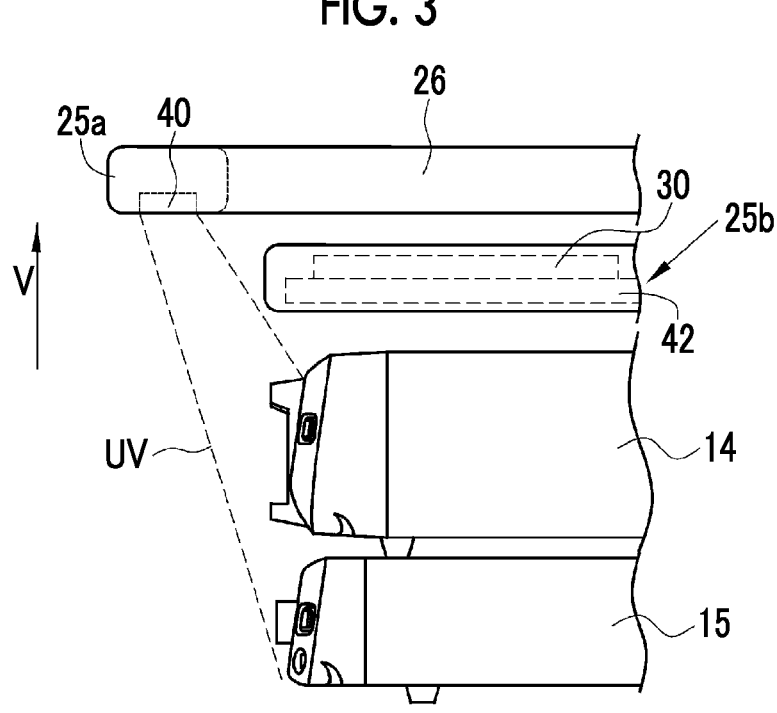
FIG. 3 is a side view of the light source device, the processor device, and the placement portion, on which the light source device and the processor device are mounted, in a case where the handle portion is provided with the ultraviolet ray source portion.

The endoscope cart 20 is provided with an ultraviolet ray source portion that irradiates the instrument for an endoscope with ultraviolet rays. Specifically, as shown in FIGS. 2 and 3, an ultraviolet ray source portion 40 is provided with respect to the handle portion 25a. The ultraviolet ray source portion 40 is provided at a lower surface of the handle portion 25a and irradiates the light source device 14 or the processor device 15 with ultraviolet rays UV. It is preferable that the ultraviolet ray source portion 40 is provided such that at least one of an operation panel 14a of the light source device 14 or an operation panel 15a of the processor device 15 is irradiated with the ultraviolet rays UV (irradiated with the ultraviolet rays UV from an upper side or an obliquely upper side). The ultraviolet rays UV are used for bacteria-elimination or sterilization of an endoscope instrument, as will be described later. Note that the upper side means an upward direction with respect to a vertical direction V (refer to FIGS. 2 and 3) and the obliquely upper side means an oblique direction inclined with respect to the vertical direction V at a predetermined angle.

Note that the operation panel 14a is a touch panel or the like and is used to perform various setting operations with respect to the light source device 14 by being directly touched and pressed by a user such as a doctor, a technologist, and a nurse. The same applies to the operation panel 15a. In addition, the endoscope cart 20 may be provided with a motion sensor (not shown) and the light source device 14 and the processor device 15 may be automatically irradiated with the ultraviolet rays UV from the ultraviolet ray source portion 40 in a case where the motion sensor detects that there is no person in the vicinity of the endoscope cart 20.

Figure 4:
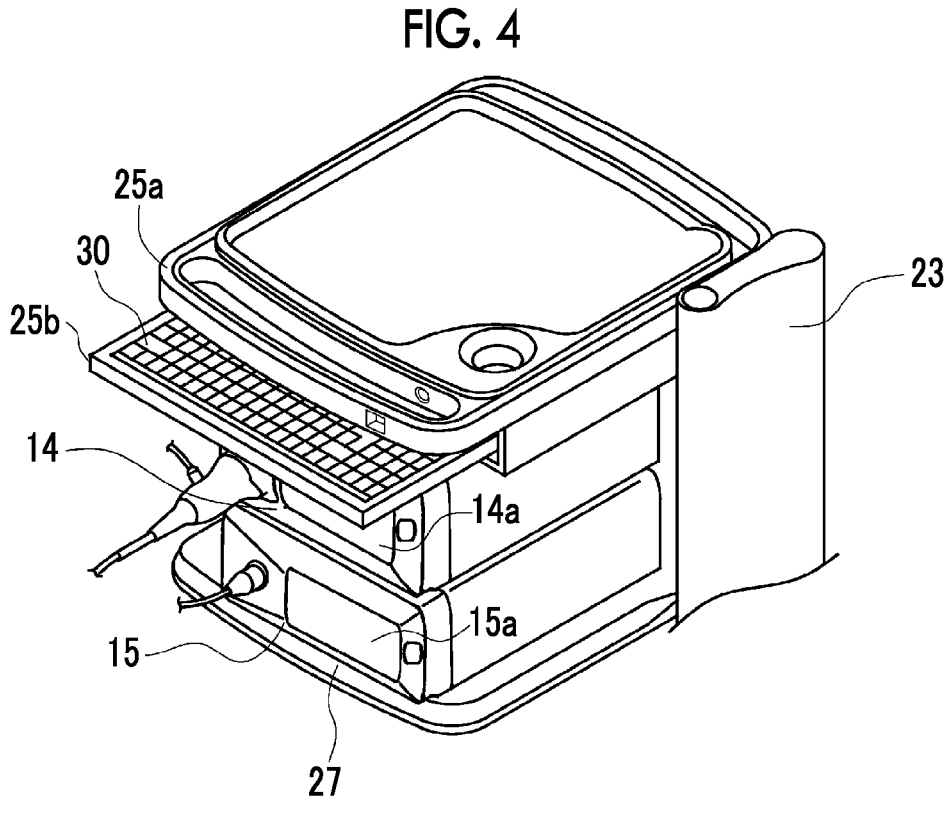
FIG. 4 is a perspective view of the light source device, the processor device, and the placement portion, on which the light source device and the processor device are mounted, in a case where a drawer portion is provided with an ultraviolet ray source portion.
Figure 5:
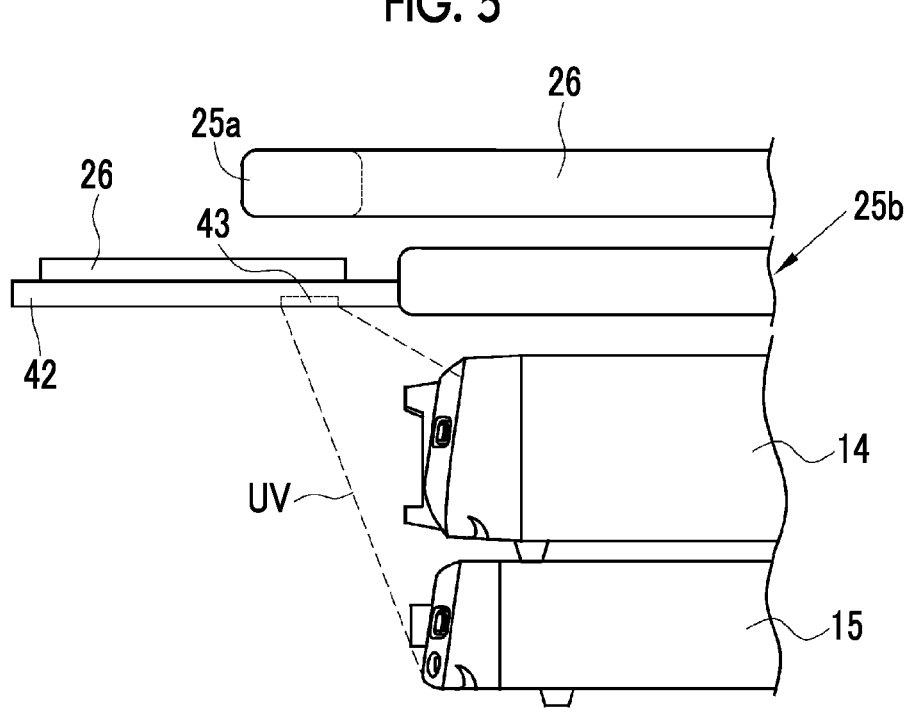
FIG. 5 is a side view of the light source device, the processor device, and the placement portion, on which the light source device and the processor device are mounted, in a case where the drawer portion is provided with the ultraviolet ray source portion.

In addition, as shown in FIGS. 4 and 5, in a case where the drawer portion 25b includes a sliding plate 42 that is movable between a storage position and a pull-out position to which the sliding plate 42 is pulled out from the storage position, an ultraviolet ray source portion 43 is provided with respect to the sliding plate 42. The ultraviolet ray source portion 43 is provided at a lower surface of the sliding plate 42, and in a case where the sliding plate 42 is at the pull-out position, the light source device 14 or the processor device 15 is irradiated with the ultraviolet rays UV. It is preferable that the ultraviolet ray source portion 43 is provided such that at least one of the operation panel 14a of the light source device 14 or the operation panel 15a of the processor device 15 is irradiated with the ultraviolet rays UV (irradiated with the ultraviolet rays UV from an upper side or a diagonally upper side).

Figure 6:
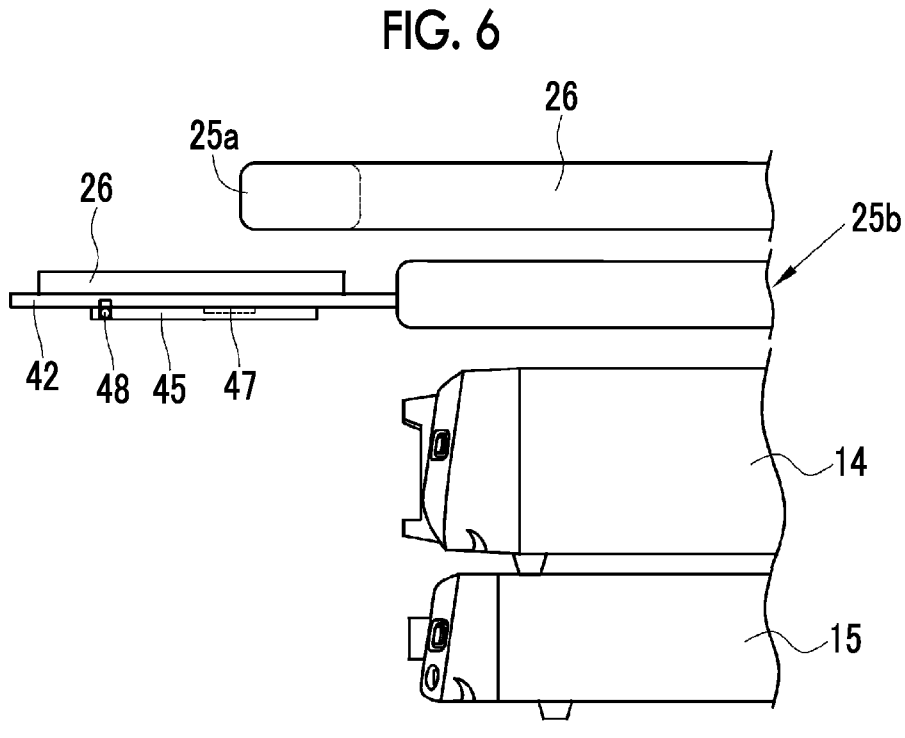
FIG. 6 is a side view of the light source device, the processor device, and the placement portion, on which the light source device and the processor device are mounted, in a case where a rotary panel provided with an ultraviolet ray source portion is in a closed state.
Figure 7:
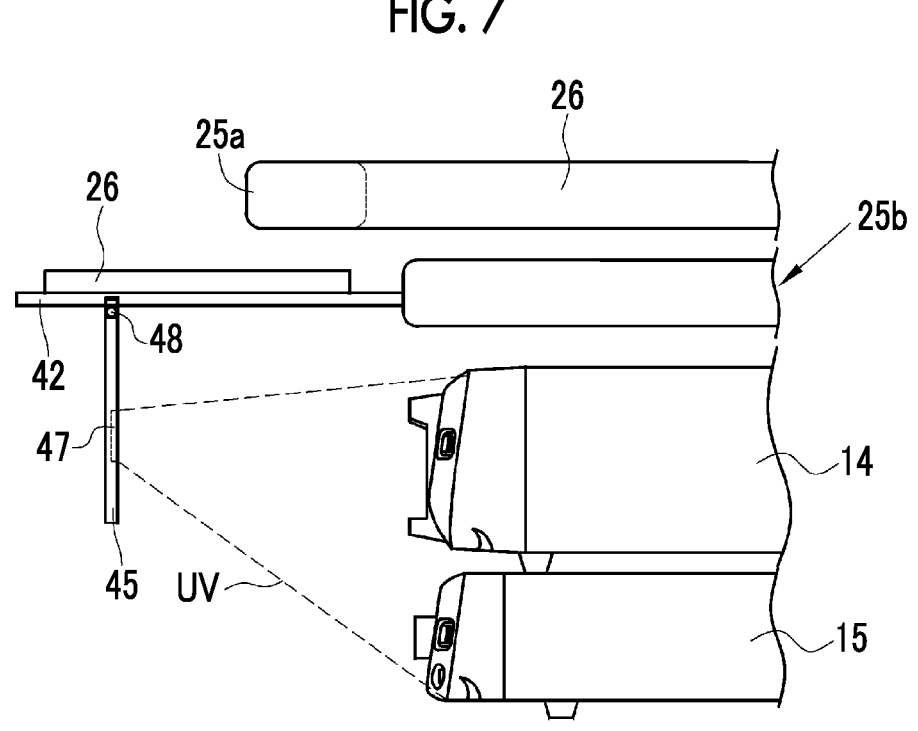
FIG. 7 is a side view of the light source device, the processor device, and the placement portion, on which the light source device and the processor device are mounted, in a case where the rotary panel provided with the ultraviolet ray source portion is in an opened state.
Figures 8, 9:
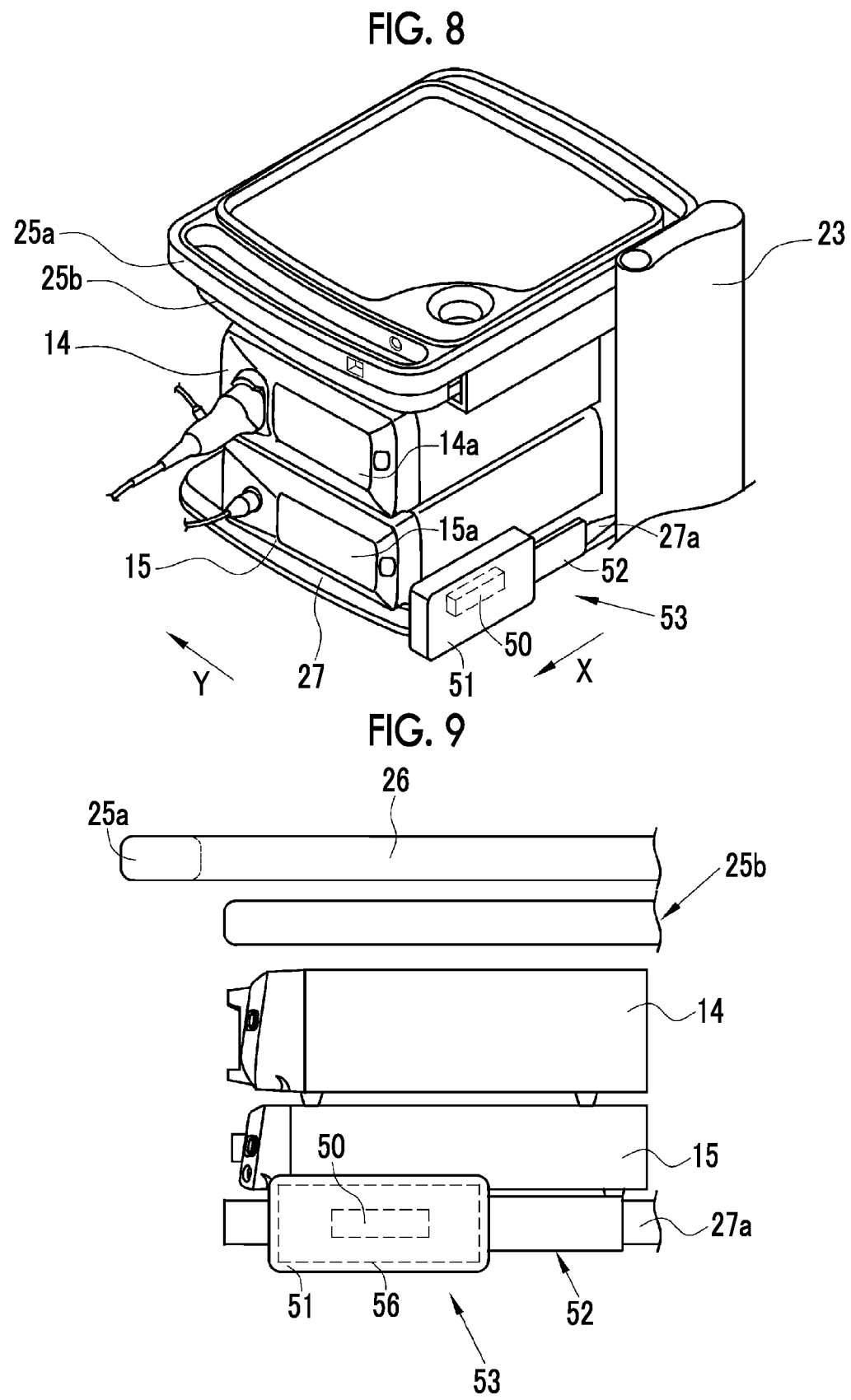
FIG. 8 is a perspective view of the light source device, the processor device, and the placement portion, on which the light source device and the processor device are mounted, in a case where an ultraviolet ray source unit attached to the placement portion is in a not-in-use state.
FIG. 9 is a side view of the light source device, the processor device, and the placement portion, on which the light source device and the processor device are mounted, in a case where the ultraviolet ray source unit attached to the placement portion is in the not-in-use state.
Figure 10:
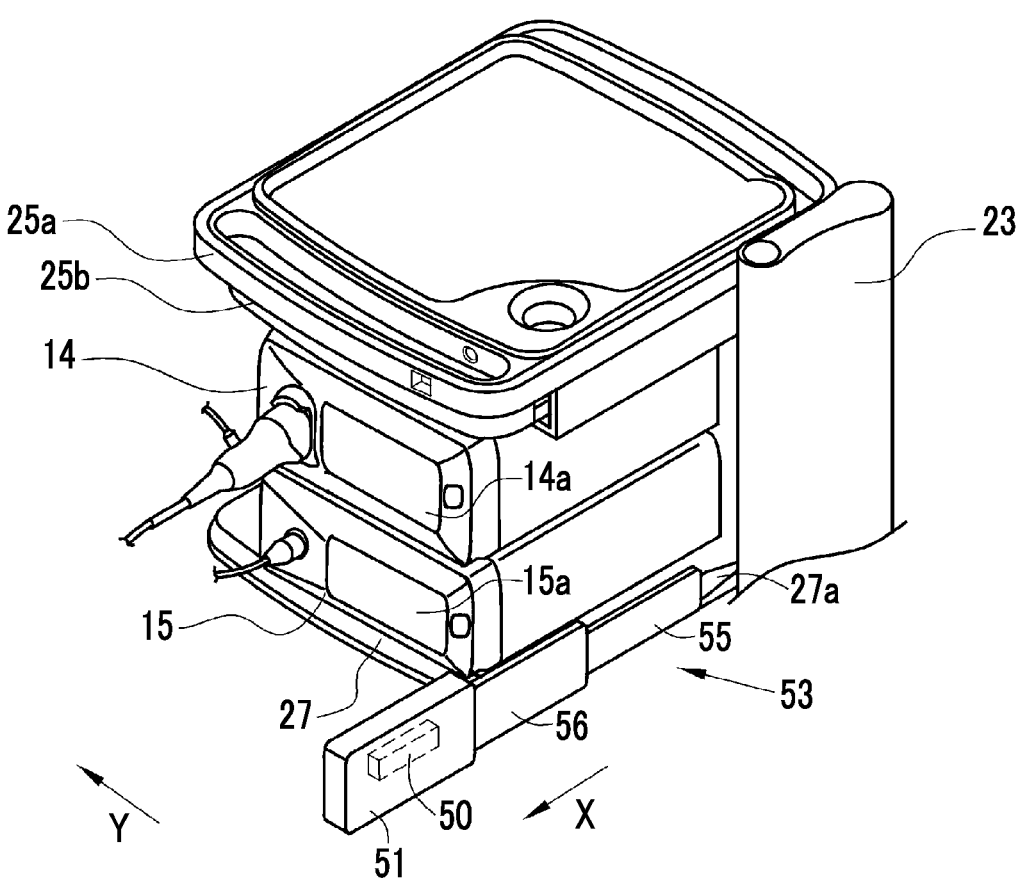
FIG. 10 is a perspective view of the light source device, the processor device, and the placement portion, on which the light source device and the processor device are mounted, in the case of a stage in which the ultraviolet ray source unit attached to the placement portion transitions into an in-use state.
Figure 11:
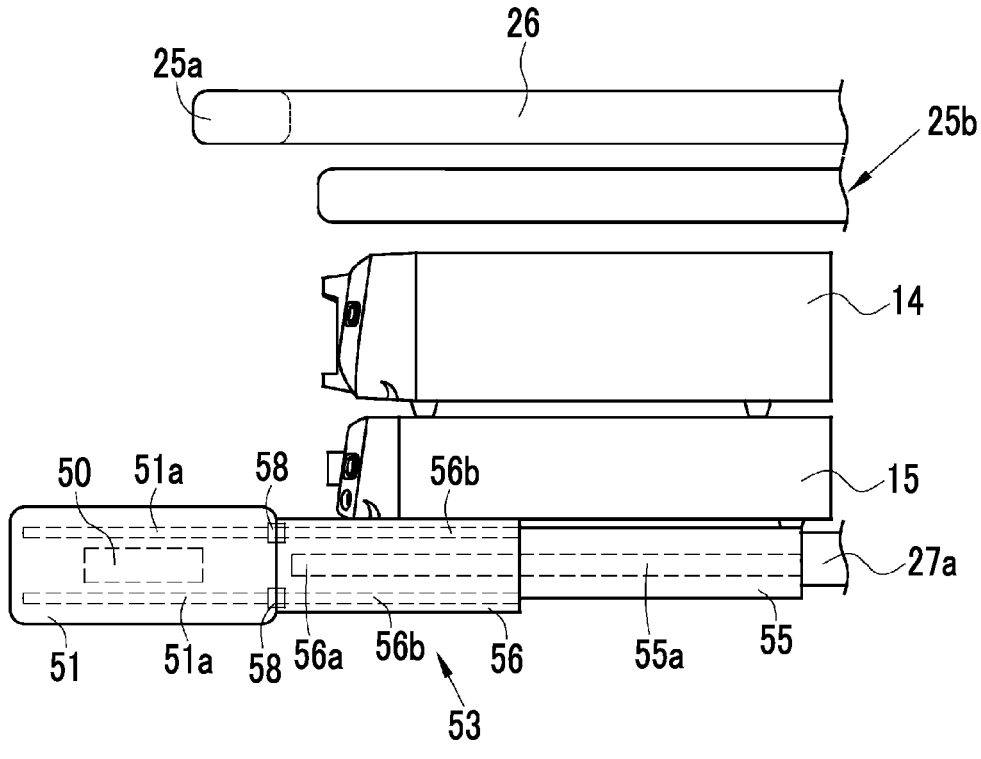
FIG. 11 is a side view of the light source device, the processor device, and the placement portion, on which the light source device and the processor device are mounted, in the case of the stage in which the ultraviolet ray source unit attached to the placement portion transitions into the in-use state.
Figure 12:
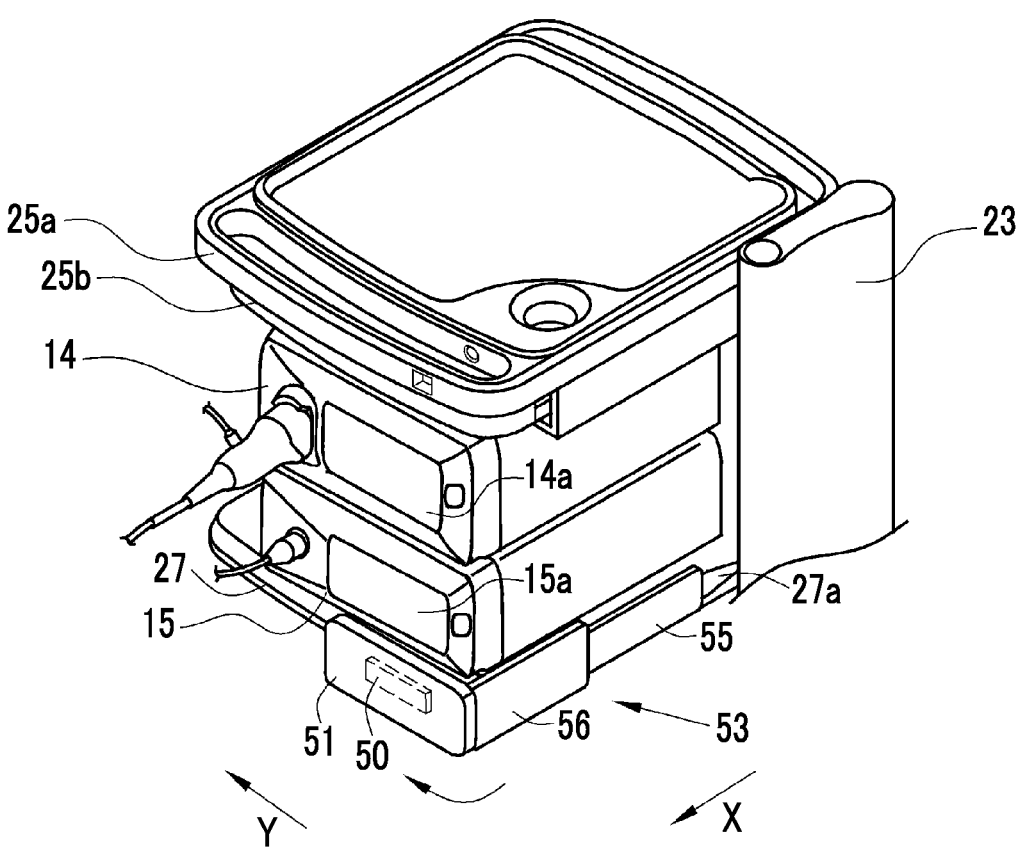
FIG. 12 is a perspective view of the light source device, the processor device, and the placement portion, on which the light source device and the processor device are mounted, in a case where the ultraviolet ray source unit attached to the placement portion is in the in-use state.
Figure 13:
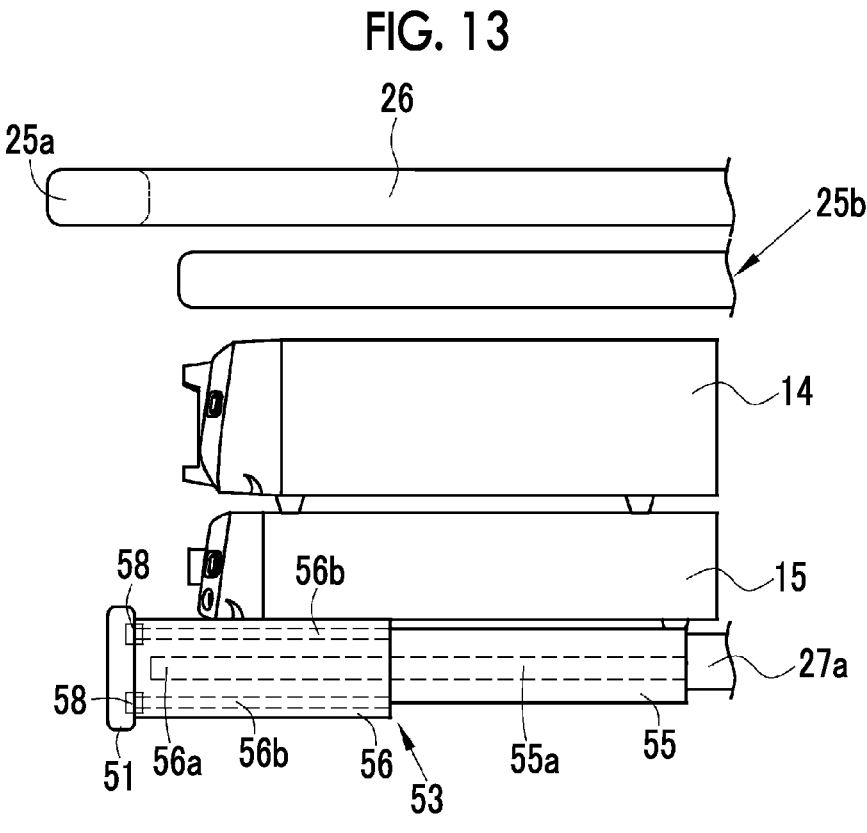
FIG. 13 is a side view of the light source device, the processor device, and the placement portion, on which the light source device and the processor device are mounted, in a case where the ultraviolet ray source unit attached to the placement portion is in the in-use state.

In addition, as shown in FIGS. 6 and 7, in a case where the lower surface of the sliding plate 42 is provided with a rotary panel 45 that is rotatable between a closing position (a state as shown in FIG. 6) and an opening position (a state as shown in FIG. 7), the rotary panel 45 may be provided with an ultraviolet ray source portion 47. The rotary panel 45 is rotatably attached to the lower surface of the sliding plate 42 by means of a hinge 48. In a case where the rotary panel 45 is at the closing position, the rotary panel 45 is in a state of abutting the sliding plate 42 while being parallel with the sliding plate 42. In a case where the rotary panel 45 is at the closing position, the sliding plate 42 can be moved to the storage position. Meanwhile, in a case where the rotary panel 45 is at the opening position, the rotary panel 45 is in a state of being inclined with respect to the sliding plate 42 at a certain angle (an angle larger than 0 degrees), so that the light source device 14 or the processor device 15 can be irradiated with the ultraviolet rays UV from the ultraviolet ray source portion 47.

It is preferable that the angle of the rotary panel 45 at the opening position is set such that at least one of the operation panel 14a of the light source device 14 or the operation panel 15a of the processor device 15 is irradiated with the ultraviolet rays UV. For example, in the case of FIG. 7, the angle of the rotary panel 45 with respect to the sliding plate 42 is approximately 90 degrees, and the ultraviolet ray source portion 47 is in a state of being faced by the operation panels 14a and 15a.

In addition, as shown in FIGS. 8 to 15, the endoscope cart 20 may be provided with an ultraviolet ray source unit 53 composed of a light source housing 51 that is provided with an ultraviolet ray source portion 50 and a light source holding portion 52 that holds the light source housing 51, that is movable in a first direction, and that is rotatable toward a second direction orthogonal to the first direction. Specifically, it is preferable that the ultraviolet ray source unit 53 is provided along a side surface 27a of the shelf plate 27. For example, the light source holding portion 52 is attached to a side surface of the shelf plate 27. The light source holding portion 52 includes a fixed plate 55 that is fixed and attached to the side surface 27a of the shelf plate and the light source housing 51 and an extension plate 56 for extension of the position of the light source housing 51 to a front surface side of the processor device 15. Note that the ultraviolet ray source unit 53 is composed of the three members which are the light source housing 51, the fixed plate 55, and the extension plate 56. However, the ultraviolet ray source unit 53 may be composed of only two members which are the light source housing 51 and the fixed plate 55.

Regarding the ultraviolet ray source unit 53, it is preferable that the light source housing 51 is movable with respect to a depth direction X (the first direction) and is rotatable with respect to a width direction Y (the second direction) orthogonal to the depth direction X. Therefore, the fixed plate 55 is provided with one rail 55a into which one long protrusion portion 56a provided on the extension plate 56 is inserted. By means of the protrusion portion 56a and the rail 55a, the extension plate 56 is movable between an extension plate extension position for extension from the fixed plate 55 and an extension plate storage position (refer to FIG. 9) at which a portion of the fixed plate 55 is stored.

Further, the extension plate 56 is provided with two rails 56b into which two long protrusion portions 51a provided on both end portions of the light source housing 51 are inserted. By means of the protrusion portions 51a and the rails 56b, the light source housing 51 is movable between a housing extension position (refer to FIG. 11) after extension from the extension plate 56 and a housing storage position at which the extension plate 56 is stored. In addition, between the light source housing 51 and the extension plate 56, rotational movement portions 58 for making the light source housing 51 rotatable to the width direction Y from the depth direction X or rotatable to the depth direction X from the width direction are provided (refer to FIGS. 12 and 13).

In a case where the ultraviolet ray source unit 53 is in a not-in-use state (refer to FIGS. 8 and 9) in which irradiation with the ultraviolet rays is not performed, the extension plate 56 is at the extension plate storage position and the light source housing 51 is at the housing storage position. Meanwhile, in the case of an in-use state in which irradiation with the ultraviolet rays is performed, first, the extension plate 56 is moved to the extension plate extension position and the light source housing 51 is moved to the housing extension position (refer to FIGS. 10 and 11). Then, the light source housing 51 is rotated from the depth direction X to the width direction Y by means of the rotational movement portions 58. Accordingly, the ultraviolet ray source portion 50 in the light source housing 51 faces the operation panel 15a of the processor device 15 (see FIGS. 12 and 13). In this state, the operation panel 15a is irradiated with the ultraviolet rays UV. Note that the ultraviolet ray source unit 53 may be attached to the columns 23 and 24 and the light source device 14 may be irradiated with the ultraviolet rays UV with the light source housing 51 being moved or rotated in the same manner as that described above.

Figure 14:
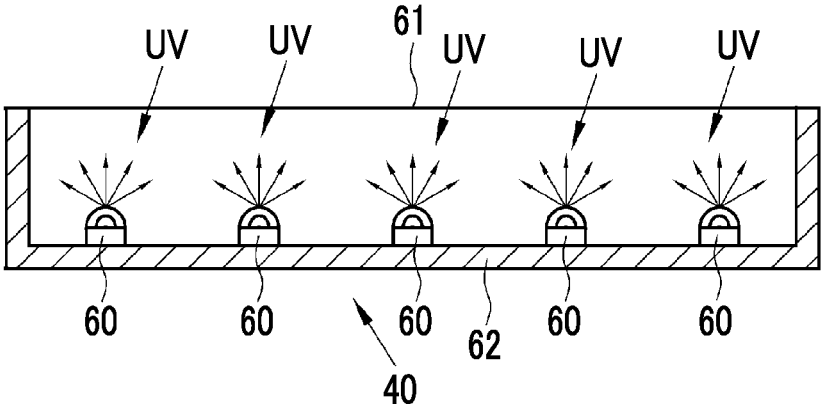
FIG. 14 is a cross-sectional view of an ultraviolet ray source portion including an ultraviolet ray source.

It is preferable that the ultraviolet ray source portion 40 includes, as shown in FIG. 14, an ultraviolet ray source 60 that emits the ultraviolet rays UV and an emission portion 61 through which the ultraviolet rays UV are emitted toward the instrument for an endoscope. The emission portion 61 is formed of a transparent member that transmits light at one surface of a light source box 62 having an approximately rectangular parallelepiped-like shape. With the ultraviolet ray source 60 and the emission portion 61 facing each other, the instrument for an endoscope is irradiated with the ultraviolet rays UV from the ultraviolet ray source 60 that pass through the emission portion 61. In addition, it is preferable that a plurality of (five in FIG. 14) the ultraviolet ray sources 60 are disposed at predetermined intervals in the light source box 62. Note that it is preferable that the other ultraviolet ray source portions 43, 47, and 50 also have the same configuration as the ultraviolet ray source portion 40.

Figure 15:
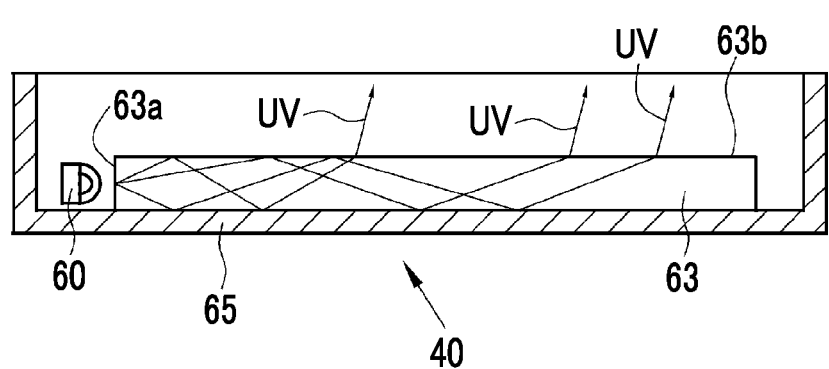
FIG. 15 is a cross-sectional view of an ultraviolet ray source portion including an ultraviolet ray source and a light guide plate.

In addition, it is preferable that the ultraviolet ray source portion 40 includes, as shown in FIG. 15, the ultraviolet ray source 60 that emits the ultraviolet rays UV, a light guide plate 63 that guides the ultraviolet rays UV emitted from the ultraviolet ray source 60, and an emission portion 64 through which the ultraviolet rays UV are emitted toward the instrument for an endoscope. The light guide plate 63 includes an incident surface 63a and an emission surface 63b. The ultraviolet ray source 60 is disposed to face the incident surface 63a of the light guide plate 63. The ultraviolet rays UV from the ultraviolet ray source 60 that are incident on the incident surface 63a are reflected or the like inside and then are emitted through the emission surface 63b. The emission portion 64 is formed of a transparent member that transmits light at one surface of a light source box 65 having an approximately rectangular parallelepiped-like shape. With the light guide plate 63 and the emission portion 64 facing each other, the instrument for an endoscope is irradiated with the ultraviolet rays UV that are emitted through the emission surface 63b of the light guide plate and that pass through the emission portion 64.

The ultraviolet ray source 60 is any of an excimer lamp or a light emitting diode (LED) for ultraviolet rays. The excimer lamp preferably emits, as ultraviolet rays, first ultraviolet rays having a peak wavelength of 222 nm (±10 nm) and a wavelength range of 200 nm to 280 nm. The transmittance of the first ultraviolet rays with respect to a living body is lower than the transmittance of ultraviolet rays (specific ultraviolet rays) at a wavelength of 254 nm (at which the intensity of light is high) with respect to a living body. For example, the transmittance of the first ultraviolet rays with respect to a cornea of an eye (the ratio of light absorbed by the cornea to light incident on the cornea) is 0.01 and the transmittance of the specific ultraviolet rays with respect to the cornea is 30%. Therefore, the first ultraviolet rays have an ability for sterilization and inactivation of viruses, which is inherent in ultraviolet rays, while being safe for the skin and eyes of humans and animals. Note that the ultraviolet rays are invisible light that cannot be recognized by a human, a visible light source may be separately provided so that visible light such as blue light is emitted. In this case, the visible light may be adjusted in density over time or may be turned on and off slowly.

It is preferable that the LED for ultraviolet rays emits second ultraviolet rays, which are deep ultraviolet rays having a wavelength range of 300 nm or less, as ultraviolet rays. Since the second ultraviolet rays have a function of destroying genetic information of a virus or a bacterium, the second ultraviolet rays have a sterilization effect on water, air, or the like. For example, the second ultraviolet rays have a high sterilization effect against the human coronavirus (HCoV-229E), as a virus. In addition, it is preferable that the LED for ultraviolet rays has a function such as a waterproofing function or a heat radiation function. The influence of the LED for ultraviolet rays on the environment is smaller than that of a mercury lamp.

Figure 16:
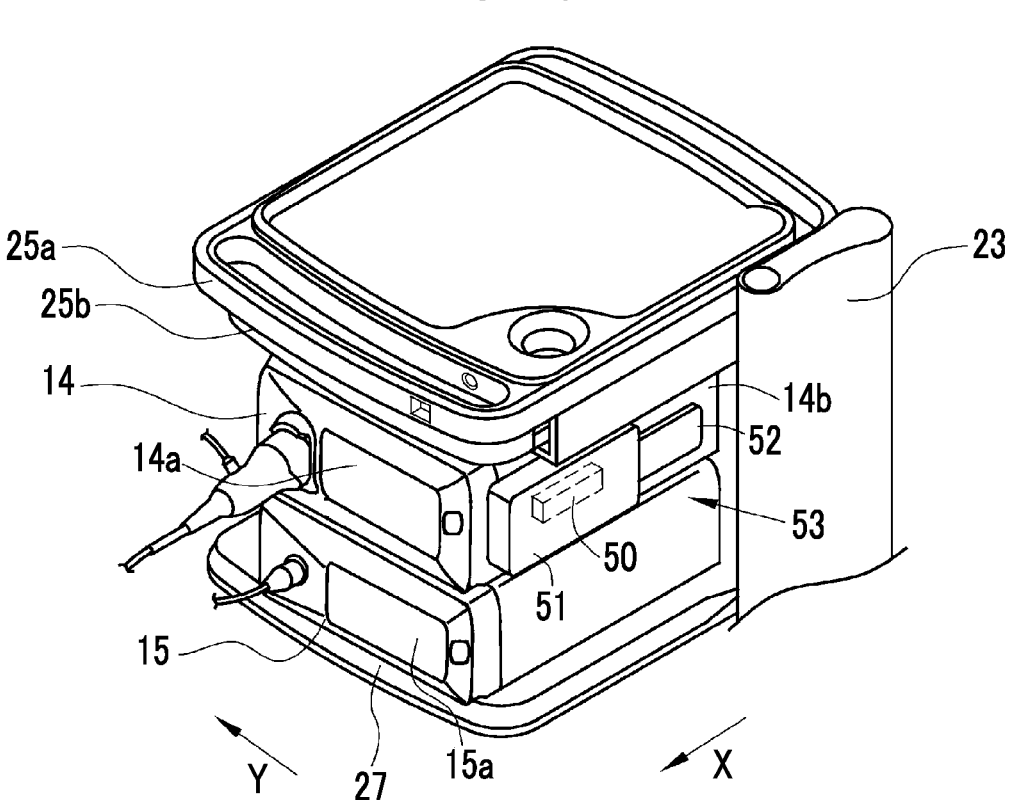
FIG. 16 is a perspective view of the light source device, the processor device, and the placement portion, on which the light source device and the processor device are mounted, in a case where the ultraviolet ray source unit attached to the light source device is in the not-in-use state.
Figure 17:
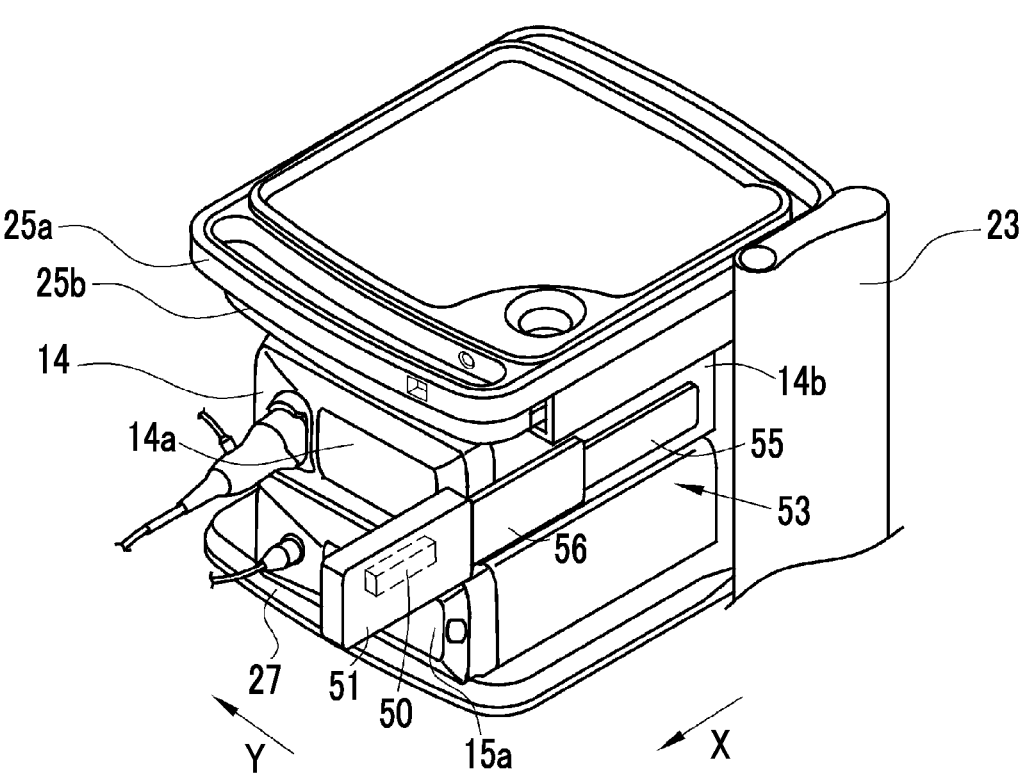
FIG. 17 is a perspective view of the light source device, the processor device, and the placement portion, on which the light source device and the processor device are mounted, in the case of a stage in which the ultraviolet ray source unit attached to the light source device transitions from the in-use state.
Figure 18:
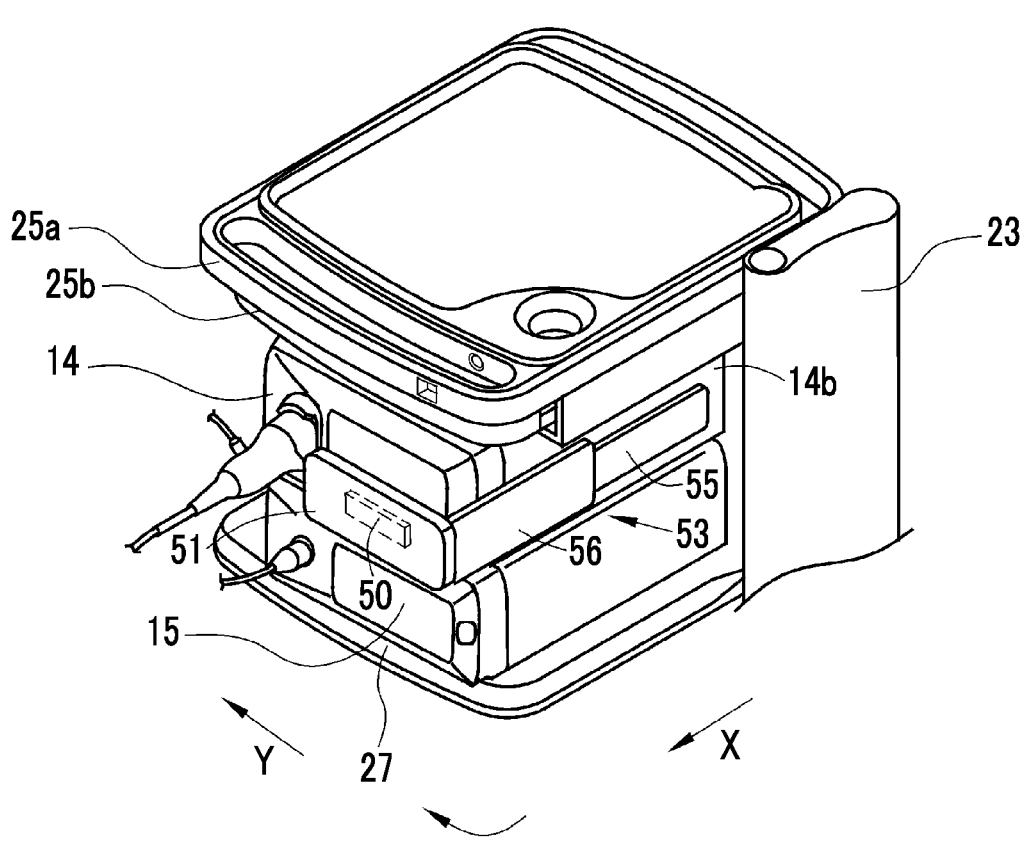
FIG. 18 is a perspective view of the light source device, the processor device, and the placement portion, on which the light source device and the processor device are mounted, in a case where the ultraviolet ray source unit attached to the light source device is in the in-use state.

Note that although the endoscope cart 20 is provided with the ultraviolet ray source unit in the above-described embodiment, the ultraviolet ray source unit 53 may be attached to another instrument for an endoscope. For example, as shown in FIGS. 16 to 18, the ultraviolet ray source unit 53 may be attached to a side surface 14b of the light source device 14. In this case, in the case of a not-in-use state (refer to FIG. 16) in which irradiation with the ultraviolet rays is not performed, the extension plate 56 is at the extension plate storage position and the light source housing 51 is at the housing storage position. Meanwhile, in the case of an in-use state in which irradiation with the ultraviolet rays is performed, first, the extension plate 56 is moved to the extension plate extension position and the light source housing 51 is moved to the housing extension position (refer to FIG. 17). Then, the light source housing 51 is rotated from the depth direction X to the width direction Y by means of the rotational movement portions 58. Accordingly, the ultraviolet ray source portion 50 in the light source housing 51 faces the operation panel 14a of the light source device 14 (see FIG. 18). In this state, the operation panel 14a is irradiated with the ultraviolet rays UV. The ultraviolet ray source unit 53 may be attached to the processor device 15 to irradiate the processor device 15 with the ultraviolet rays UV. In addition, it is preferable that the ultraviolet ray source unit enters an in-use state in which irradiation with the ultraviolet rays is performed in a preparation stage before endoscopy or a test-ended stage after the end of the endoscopy.

Figure 19:
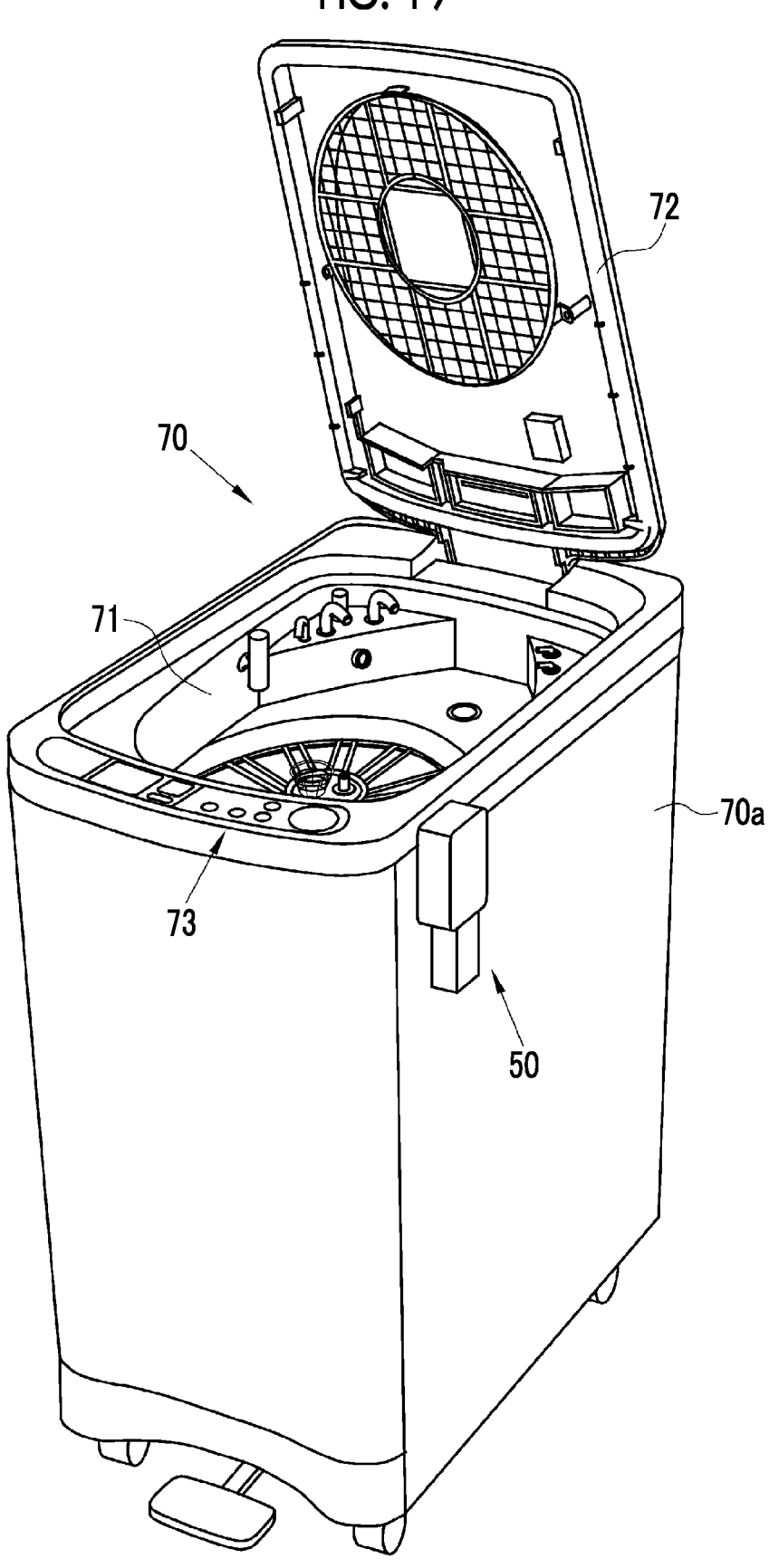
FIG. 19 is a perspective view of a cleaning and disinfecting apparatus.
Figure 20:
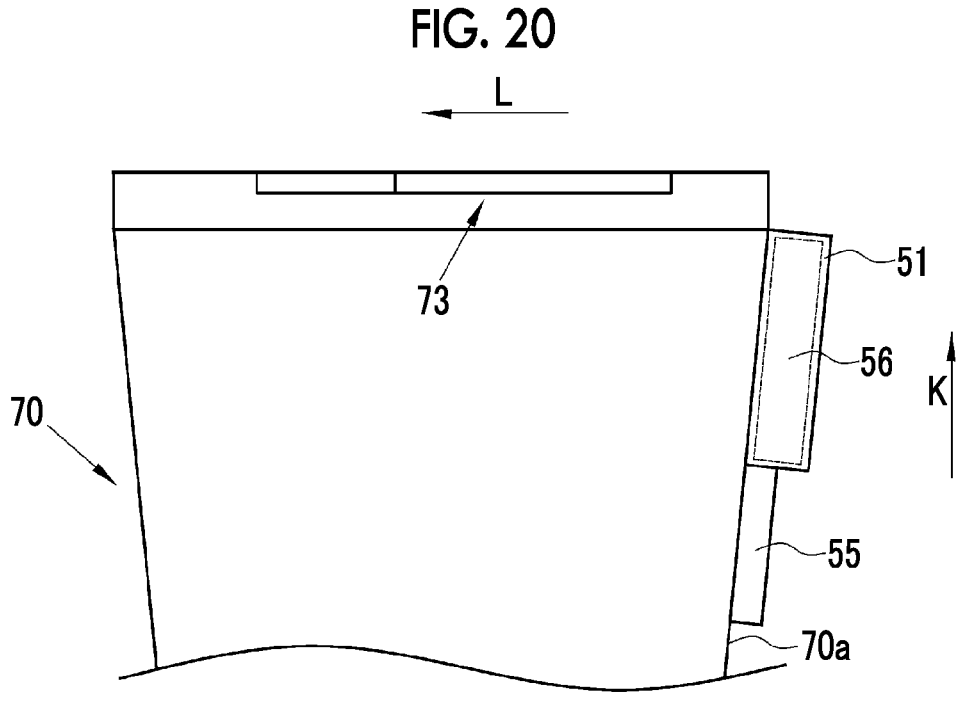
FIG. 20 is a perspective view of the cleaning and disinfecting apparatus in a case where the ultraviolet ray source unit attached to the cleaning and disinfecting apparatus is in the not-in-use state.
Figure 21:
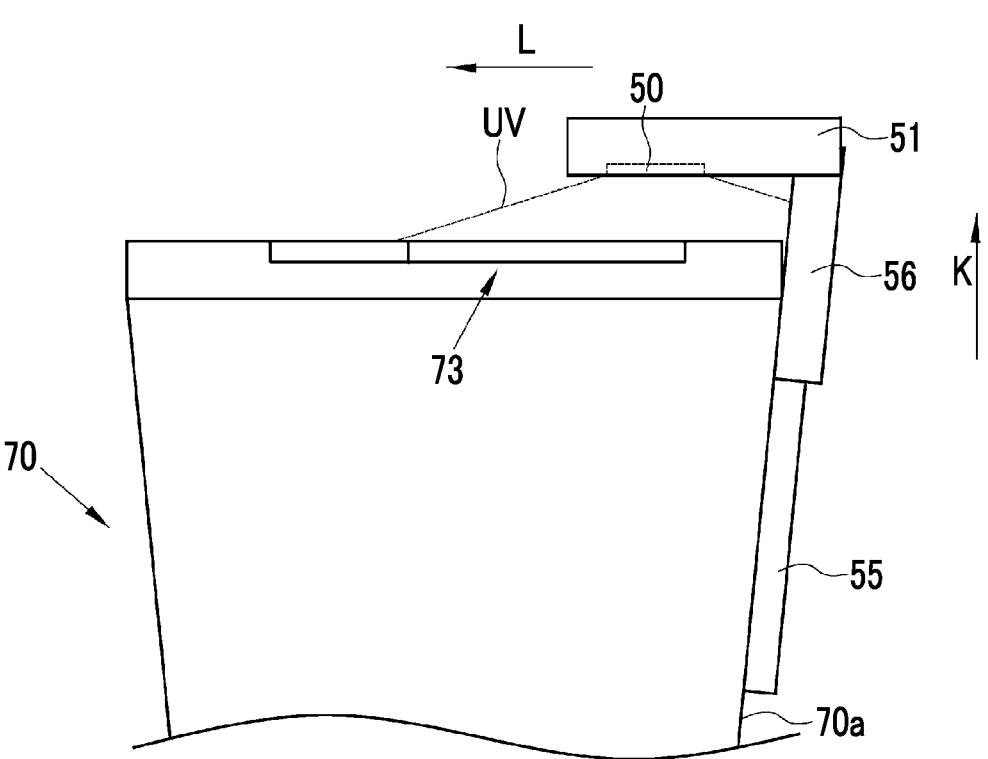
FIG. 21 is a perspective view of the cleaning and disinfecting apparatus in a case where the ultraviolet ray source unit attached to the cleaning and disinfecting apparatus is in the in-use state.

In addition, as shown in FIGS. 19 to 21, the ultraviolet ray source unit 53 may be attached to a side surface 70a of a cleaning and disinfecting apparatus 70. The cleaning and disinfecting apparatus 70 includes a storage portion 71 in which an endoscope is stored and cleaned or disinfected, a lid 72 used to airtightly close the storage portion 71, and an operation panel 73 used to perform an operation such as a cleaning start operation. In this case, in the case of a not-in-use state (refer to FIG. 20) in which irradiation with the ultraviolet rays is not performed, the extension plate 56 is at the extension plate storage position and the light source housing 51 is at the housing storage position. Meanwhile, in the case of an in-use state in which irradiation with the ultraviolet rays is performed, first, the extension plate 56 is moved to the extension plate extension position and the light source housing 51 is moved to the housing extension position. Then, the light source housing 51 is rotated from a height direction K (the first direction) to a width direction L (the second direction) by means of the rotational movement portion 58. Accordingly, the ultraviolet ray source portion 50 in the light source housing 51 faces the operation panel 73 (see FIG. 21). In this state, the operation panel 73 is irradiated with the ultraviolet rays UV.

APPENDIX 1

A cleaning and disinfecting apparatus including an ultraviolet ray source portion that performs irradiation with ultraviolet rays.

APPENDIX 2

A cleaning and disinfecting apparatus according to Appendix 1, further including an ultraviolet ray source unit composed of a light source housing that is provided with the ultraviolet ray source portion and a light source holding portion that holds the light source housing, that is movable in a first direction, and that is rotatable toward a second direction orthogonal to the first direction.

EXPLANATION OF REFERENCES

10: endoscope system
12: endoscope
12a: soft portion
12b: operation portion
12c: bendable portion
12d: distal end portion
12e: angle knob
12f: cord
14: light source device
14a: operation panel
14b: side surface
15: processor device
15a: operation panel
16: display
20: endoscope cart
21: frame pedestal portion
22: caster
22a: stop lever
23, 24: column
25a: handle portion
25b: drawer portion
26: top plate
27, 28: shelf plate
27a: side surface
29: stand
30: keyboard
31: hanger stand
31a: stand member
31b: stand member
32: hanger
40, 43, 47, 50: ultraviolet ray source portion 42: sliding plate
45: rotary panel
48: hinge
51: light source housing
51*a*: protrusion portion
52 light source holding portion
53: ultraviolet ray source unit
55: fixed plate
55*a*: rail
56: extension plate
56*a*: protrusion portion
56*b*: rail
58: rotational movement portion
60: ultraviolet ray source
61: emission portion
62: light source box
63: light guide plate
63*a*: Incident surface
63*b*: emission surface
64: emission portion
65: light source box
70: cleaning and disinfecting apparatus
70*a*: side surface
71: storage portion
72: lid
73: operation panel

What is claimed is:

1. An endoscope cart comprising:
a placement portion on which an instrument for an endoscope is placed in a state of being exposed outside;
an ultraviolet ray source portion that irradiates the instrument for an endoscope in the state of being exposed outside, with ultraviolet rays;
a top plate that is provided above the placement portion;
a drawer portion that is provided between the top plate and the placement portion and that includes a sliding plate movable between a storage position and a pull-out position to which the sliding plate is pulled out from the storage position; and
a rotary panel that is attached to the sliding plate to be rotatable between a closing position and an opening position,
wherein the ultraviolet ray source portion is provided on the rotary panel.

2. The endoscope cart according to claim 1, further comprising:
a handle portion provided at a front portion of the top plate.

3. The endoscope cart according to claim 1,
wherein the ultraviolet ray source portion is provided on the rotary panel attached to the sliding plate.

4. The endoscope cart according to claim 1,
wherein the instrument for an endoscope is irradiated with the ultraviolet rays from at least one of an upper side or an obliquely upper side.

5. The endoscope cart according to claim 1, wherein the ultraviolet ray source unit further comprising:
a light source housing that is provided with the ultraviolet ray source portion; and
a light source holding portion that holds the light source housing, that is movable in a first direction, and that is rotatable toward a second direction orthogonal to the first direction.

6. The endoscope cart according to claim 1,
wherein the ultraviolet ray source portion includes an ultraviolet ray source that emits the ultraviolet rays and an emission portion through which the ultraviolet rays are emitted toward the instrument for an endoscope, and
the ultraviolet ray source and the emission portion face each other.

7. The endoscope cart according to claim 1,
wherein the ultraviolet ray source portion includes an ultraviolet ray source that emits the ultraviolet rays, a light guide plate that guides the ultraviolet rays emitted from the ultraviolet ray source, and an emission portion through which the ultraviolet rays are emitted toward the instrument for an endoscope, and
the light guide plate and the emission portion face each other.

8. The endoscope cart according to claim 6,
wherein the ultraviolet ray source is any of an excimer lamp or an LED.

9. The endoscope cart according to claim 1,
wherein the instrument for an endoscope is any one or a combination of two or more of a processor device, a light source device, a water supply device, an air supply device, or a treatment tool power source.

* * * * *